United States Patent [19]
Child et al.

[11] Patent Number: 5,382,746
[45] Date of Patent: Jan. 17, 1995

[54] REMOVAL OF LIGHT ASO IN HF ALKYLATION PROCESS

[75] Inventors: Jonathan E. Child; Tomas R. Melli, both of Sewell, N.J.; Sergei Yurchak, Media, Pa.

[73] Assignee: Mobil Oil Corporation, Fairfax, Va.

[21] Appl. No.: 117,274

[22] Filed: Sep. 7, 1993

Related U.S. Application Data

[63] Continuation-in-part of Ser. No. 991,918, Dec. 17, 1992, Pat. No. 5,262,579, Ser. No. 991,919, Dec. 17, 1992, Pat. No. 5,264,650, Ser. No. 991,920, Dec. 17, 1992, Pat. No. 5,264,651, Ser. No. 991,921, Dec. 17, 1992, Pat. No. 5,264,652, and Ser. No. 991,922, Dec. 17, 1992, Pat. No. 5,276,243, each is a continuation-in-part of Ser. No. 833,684, Feb. 11, 1992, Pat. No. 5,191,150.

[51] Int. Cl.$^6$ ............ C07C 2/62; C07C 7/10
[52] U.S. Cl. .............. 585/802; 585/724; 585/723; 585/857
[58] Field of Search ........... 585/802, 857, 724, 723

[56] References Cited

U.S. PATENT DOCUMENTS

| | | | |
|---|---|---|---|
| 2,615,908 | 10/1952 | McCaulay et al. | 260/438 |
| 3,531,546 | 9/1970 | Hervert | 260/683.51 |
| 3,778,489 | 12/1973 | Parker et al. | 260/683.43 |
| 3,795,712 | 3/1974 | Torck et al. | 260/671 C |
| 3,856,764 | 12/1974 | Throckmorton et al. | 260/82.1 |
| 4,025,577 | 5/1977 | Siskin et al. | 260/683.51 |
| 4,099,924 | 7/1978 | Berkman et al. | 23/273 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |
| 5,191,115 | 3/1993 | Child et al. | 585/809 |
| 5,237,122 | 8/1993 | Eastman et al. | 585/709 |
| 5,262,579 | 11/1993 | Child et al. | 585/802 |
| 5,264,650 | 11/1993 | Better et al. | 585/802 |
| 5,264,651 | 11/1993 | Better et al. | 585/802 |
| 5,264,652 | 11/1993 | Child et al. | 585/802 |
| 5,276,243 | 1/1994 | Better et al. | 585/802 |

OTHER PUBLICATIONS

L. F. Albright et al., "Alkylation of Isobutane with C$^4$ Olefins" 27 *Ind. Eng. Chem. Res.*, 381–397, (1988).
1 Handbook of Petroleum Refining Processes 23–28 (R. A. Meyers, ed., 1986).

*Primary Examiner*—Asok Pal
*Attorney, Agent, or Firm*—Alexander J. McKillop; Dennis P. Santini; Robert B. Furr, Jr

[57] ABSTRACT

The present invention provides a method for separating conjunct polymers which are formed as byproducts of acid catalyzed isoparaffin-olefin alkylation and sulfolane from a mixture containing conjunct polymers, sulfolane, and hydrofluoric acid, and for minimizing accumulation of conjunct polymeric byproducts in the recycled acid catalyst.

7 Claims, 3 Drawing Sheets

REMOVAL OF LIGHT ASO IN HF ALKYLATION PROCESS

CROSS REFERENCE TO RELATED APPLICATIONS

This is a continuation-in-part of allowed application Ser. Nos. 07/991,918 (now U.S. Pat. No. 5,262,579), 07/991,919 (now U.S. Pat. No. 5,264,650), 07/991,920 (now U.S. Pat. No. 5,264,651), 07/991,921 (now U.S. Pat. No. 5,264,652) and 07/991,922 (now U.S. Pat. No. 5,276,243), all filed Dec. 17, 1992, which are continuation-in-part of application Ser. No. 07/833,684, filed Feb. 11, 1992, now U.S. Pat. No. 5,191,150.

FIELD OF THE INVENTION

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.,* 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Patent 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well the utility of liquid Bronsted acids in combination with metal halides, particularly metal fluorides.

Isoparaffin-olefin alkylation processes typically convert at least a portion of the feedstock to conjunct polymeric byproducts, which are more commonly referred to as acid soluble oil or ASO. Adding sulfolane to HF for isoparaffin-olefin alkylation complicates the problem of removing ASO from the system because the typical boiling range of the ASO brackets the boiling point of sulfolane (285° C., 545° F.). Thus sulfolane cannot be readily separated from ASO by distillation.

Allowed applications Ser. Nos. 07/991,919, 07/991,920, 07/991,921, and 07/991,922, now U.S. Pat. Nos. 5,264,650, 5,264,651, 5,264,652 and 5,276,243 as well as U.S. Pat. No. 5,191,150 teach sulfolane recovery methods which involve reducing the HF concentration in a mixture of HF, sulfolane, and ASO to less than about 30 weight percent and then gravitationally separating the resulting for a mixture to recover sulfolane. The HF-enriched stream evolved from the stripping step of these processes contains a minor amount of relatively low boiling range conjunct polymeric byproducts (also referred to as "light acid soluble oil" or "light ASO") which is recycled to the alkylation reaction zone.

Minimizing ASO concentration in the alkylation reaction zone has been found to improve isoparaffin-olefin alkylation in the presence of HF and sulfolane. Thus it would be desirable to still further improve the processes of allowed applications Ser. Nos. 07/991,919, 07/991,920, 07/991,921, and 07/991,922, now all patented as indicated above, and U.S. Pat. No. 5,191,150 by decreasing the concentration of ASO in the HF-enriched stream recycled to the alkylation reaction zone.

SUMMARY OF THE INVENTION

The present invention provides a method separating a mixture of HF, sulfolane, and conjunct polymeric byproducts formed in HF/sulfolane-catalyzed isoparaffin-olefin alkylation, which method decreases the concentration of conjunct polymeric byproducts (ASO) recycled to the alkylation reaction zone with the recycled HF. The method of the invention strips a mixture of sulfolane, ASO, and hydrofluoric acid with isoparaffin, gravitationally separates the stripped mixture containing sulfolane, ASO, and hydrofluoric acid into (a) a less dense stream containing alkylate and a first ASO fraction; and (b) a more dense stream containing sulfolane and a second ASO fraction, and then charges the enriched overhead stream from the stripper to a main product fractionator. The enriched overhead stream preferably enters the main product fractionator at a point above the hydrocarbon feed (which hydrocarbon feed comprises the overhead stream from the gravitational separator).

The present invention comprises the sequential steps of:

(a) alkylating an isoparaffin with an olefin in the presence of an alkylation catalyst comprising HF and sulfolane in an alkylation reaction zone whereby ASO byproduct is evolved;

(b) gravitationally separating effluent from said alkylation reaction zone to provide a less-dense stream containing alkylate product and unreacted isoparaffin and a more dense stream containing sulfolane, ASO, and HF;

(c) stripping HF from all or a portion of said more dense stream of step (b) with isoparaffin to provide a stripper bottoms stream containing less than about 30 percent hydrofluoric acid by weight and a stripper overhead stream containing HF, isoparaffin, and a fraction of said ASO having a lower end boiling point than the ASO containing in said more dense stream of step (b);

(d) gravitationally separating said stripper bottoms stream into a more dense sulfolane-enriched stream and a less dense conjunct polymer-enriched stream;

(e) charging said stripper overhead stream to an alkylate product fractionator;

(f) recovering an overhead stream containing isoparaffin and HF from said alkylate product fractionator;

(g) recycling said overhead stream of step (f) to said alkylation reaction zone; and (h) recovering from said alkylate product fractionator an alkylate product stream containing alkylate gasoline and a fraction of said ASO having a lower end boiling point than the ASO containing in said more dense stream of step (b).

The method finds particular utility in regenerating an HF/sulfolane catalyst used in an isoparaffin-olefin alkylation process. The hydrofluoric acid concentration of the mixture is preferably decreased by stripping. Any suitable inert stripping fluid may be employed, including normal paraffins and isoparaffins which can be charged to the stripper tower as a vapor. Isobutane and the vaporized alkylate product formed by reacting isobutane with propene and/or butene are particularly preferred stripping fluids. Two sequential stripping steps may be used, as the purity of the separated sulfolane/conjunct polymer phases improves as the hydrofluoric acid concentration decreases. If two-stage stripping is used, the enriched stripping fluid from both stripping stages is preferably charged to the product fractionator.

The surprising effects of sequentially stripping hydrofluoric acid from the mixture before gravitational separation become particularly evident as the mixture is stripped to hydrofluoric acid levels of less than about 30 weight percent. Separation improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight. In a preferred embodiment, the catalyst mixture contains from about 0.5 to about 10 weight percent water.

The conjunct polymeric byproducts of liquid acid catalyzed isoparaffin-olefin alkylation are understood to comprise a complex mixture, but the mechanism underlying the present invention is not well understood. The stripped mixture of the present invention splits the ASO between two substantially immiscible liquid phases. The ASO fraction in the more-dense phase boils generally above the normal boiling point of sulfolane, allowing the sulfolane to be recovered as the overhead stream from a distillation tower. The less-dense phase, on the other hand is enriched in ASO and may be treated further to remove sulfolane and/or for disposal. The fraction of ASO which is stripped out of the HF/sulfolane/ASO mixture in the catalyst stripper tower boils at a lower ranges of temperatures than the total ASO fraction flowing to the catalyst stripper. Accumulating this light ASO fraction is, nontheless, detrimental to catalyst performance in the alkylation riser/reactor and the present invention improves overall process performance by continuously removing light ASO from the system.

EMBODIMENTS

Figure 1:
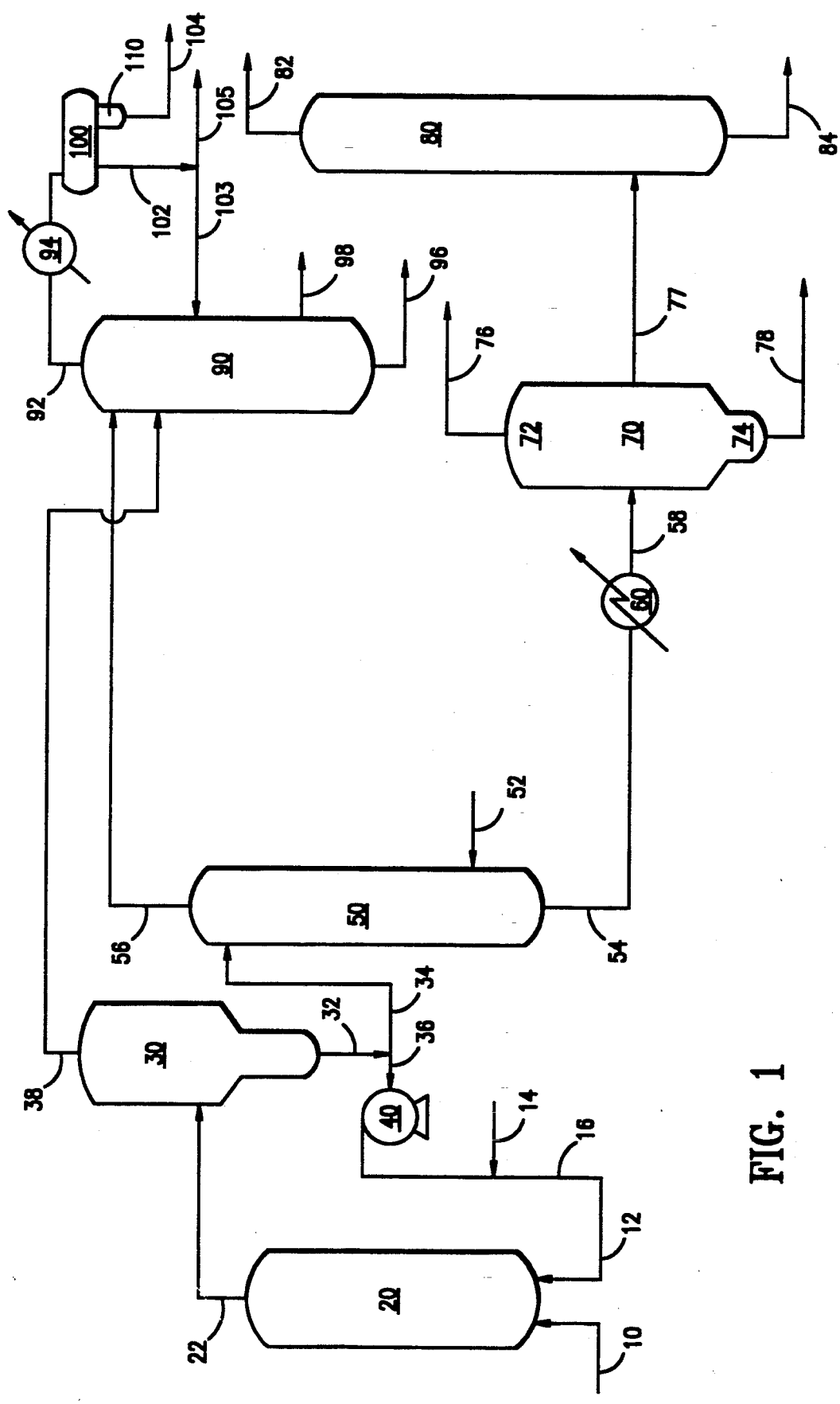
FIG. 1 is a simplified schematic diagram showing initial processing steps in the method of the invention.

Referring now to FIG. 1, mixed isoparaffin and olefin feed 10 and liquid catalyst 12 flow to riser/reactor 20. The riser/reactor effluent 22 flows to gravitational separator 30 where the effluent separates into a less dense hydrocarbon stream 38 containing alkylate and unreacted isoparaffin and a more dense catalyst stream 32 which contains HF, sulfolane, and ASO. The majority of the catalyst stream 32 recycles to riser/reactor 20 via stream 36, catalyst recycle pump 40, and stream 16. Fresh makeup HF and sulfolane enter stream 16 as required via stream 14. A minor amount of catalyst stream 32 flows to catalyst stripper 50 via stream 34. Isoparaffin (typically isobutane) from stream 52 strips HF and a lighter boiling fraction of the ASO from the catalyst mixture to produce a stripped catalyst stream 54 containing less than about 30 weight percent HF. The stripping fluid (isobutane), now enriched in HF and a lighter boiling fraction of the ASO, flows to product fractionator 90 as stream 56.

The stripped catalyst, stream 54, flows to cooler 60 from the catalyst stripper at tower temperature of about 300° F., and is cooled to about 70° F. The cooled stripped catalyst stream 58 enters gravitational separator 70 at approximately atmospheric pressure.

Two liquid phases form within gravitational separator 70. The upper, less dense phase, enriched in ASO, collects near the top 72 of gravitational separator 70, and is withdrawn through line 76 for further processing, as described below. Solids and the most dense residual hydrocarbons collect in a bottom boot 74, and are similarly withdrawn for further processing as stream 78. The lower, more dense liquid phase, enriched in sulfolane, flows out of gravitational separator 70 as stream 77 and enters a lower middle section of vacuum distillation column 80, which operates at a feed tray temperature of about 300° F. and the maximum available vacuum. The sulfolane and ASO readily separate in vacuum distillation column 80, with the sulfolane flowing overhead as stream 82 for recycle to riser/reactor 20 and the ASO leaving the column as stream 84.

Streams 38 and 56 flow to product fractionator 90, with stream 56, the isobutane stripping fluid enriched in HF and a lighter boiling fraction of the ASO, preferably entering product fractionator 90 on a tray above the feed tray for stream 38. The overhead stream 92 from product fractionator 90, enriched in isobutane and HF, condenses in overhead cooler 94 and separates into a hydrocarbon phase and an acid phase in overhead accumulator 100. The hydrocarbon phase, enriched in isobutane, leaves accumulator 100 as stream 102, and splits between reflux stream 103 and isobutane recycle stream 105. The acid phase in accumulator 100 settles in the lower boot section 110 of the accumulator and is withdrawn as stream 104 for recycle to riser/reactor 20. Alkylate product, containing a minor amount of light ASO, flows from product fractionator 90 as stream 96, while n-butane is withdrawn as side draw 98.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2–4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate more readily than mixtures having higher HF concentrations.

EXAMPLE 5

The HF/sulfolane sample of Example 5 has the following composition:
HF 62 wt. %
Sulfolane 27 wt. %
Isobutane 4 wt. %
Water 1–2 wt. %
ASO 3 wt. %
Balance to 100% other hydrocarbons. This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

Figure 2A:
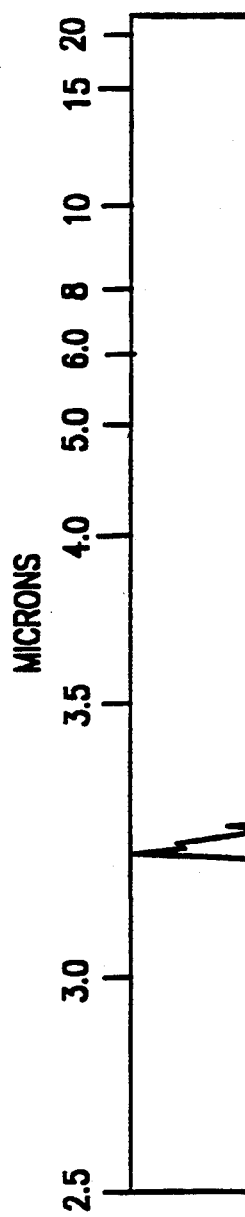
FIG. 2A shows the infrared (IR) spectrum of the conjunct polymer from the lower-density phase withdrawn from the gravitation separation step of the invention.
Figure 2B:
FIG. 2B shows the IR spectrum of the higher density phase withdrawn from the gravitational separation step of the invention.
Figure 2C:
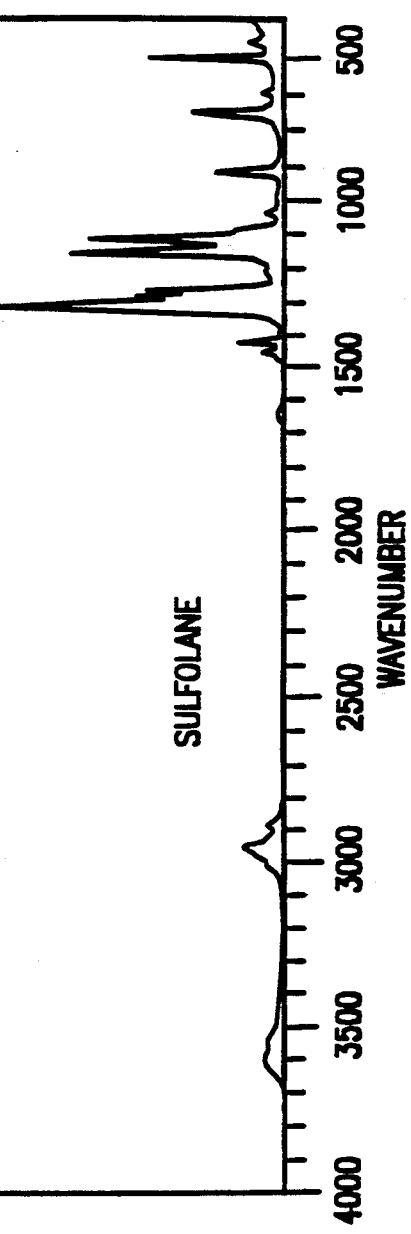
FIG. 2C shows the IR spectrum of sulfolane extracted from the higher density phase withdrawn from the gravitational step of the invention.

FIG. 2 shows the IR spectra of ASO from the lighter phase (the upper spectrum), ASO from the heavier phase (the middle spectrum) and sulfolane (the lower spectrum).

Figure 3:
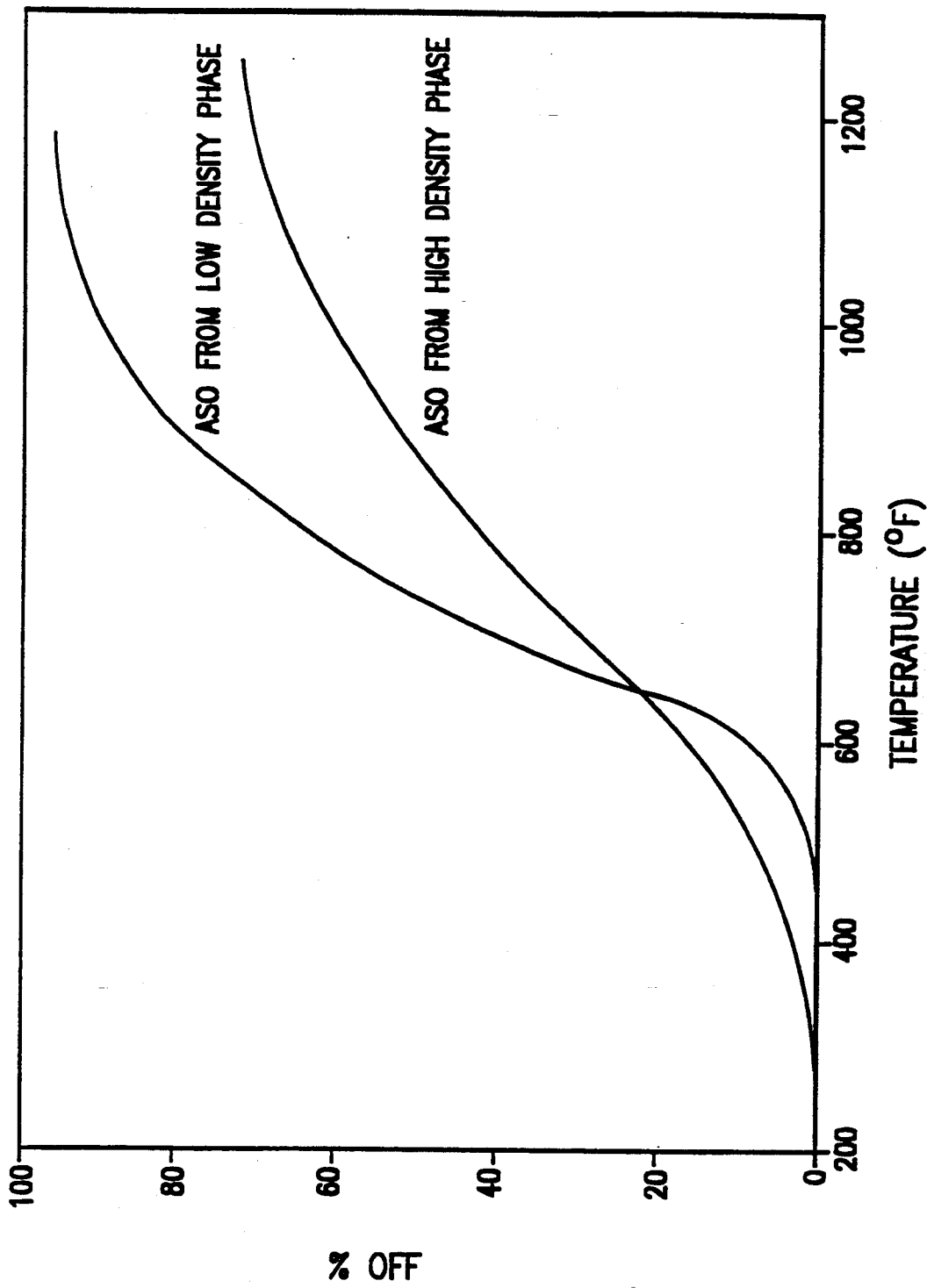
FIG. 3 shows a simulated distillation comparing the boiling ranges of components in the conjunct polymeric byproducts (also referred to herein as acid soluble oil or ASO) from the lower density phase of the gravitational separation step with the ASO from the higher density phase of the gravitational separation step of the invention.

FIG. 3 shows simulated distillations of ASO fractions from the low density phase and the high density phase from the gravitational separation step. The initial boiling point and the endpoint for the low density phase are both different from the corresponding points for the high density phase. Thus the gravitational separation splits the ASO into two fractions having different, albeit overlapping, boiling ranges.

EXAMPLE 6

The sulfolane-enriched dense phase of Example 5 is charged to a vacuum distillation column under the maximum available vacuum. The column bottom temperature is about 300° F. The overhead stream withdrawn from the distillation column is highly enriched in sulfolane while the bottoms product predominantly contains the higher boiling ASO fraction contained in the more-dense phase of Example 5.

EXAMPLE 7

A catalyst mixture containing about 65 wt. % HF, 30 wt. % sulfolane, and about 5 wt. % ASO is fed to a catalyst stripper column at a rate of about 2,000 barrels per day (BPD). The catalyst stripper column operates at about 150 psi. Isobutane (as stripping fluid) is charged to the catalyst stripper tower at a rate of about 35,000 lb/hr to strip HF and a light fraction of the ASO from the catalyst mixture. The bottom stream from the catalyst stripper tower contains approximately 82 wt. % sulfolane and the balance HF, heavy ASO, and hydrocarbons. From the top of the catalyst stripper column, about 35,000 lb/hr of isobutane, 17,000 lb/hr of HF, and 800 lb/hr of ASO at about 200° F. are sent to the an upper (stripping) section of a main product fractionator.

The principal feeds to the main product fractionator are about 950,000 lb/hr of hydrocarbon alkylation reactor effluent, which predominately comprises isobutane with about 15 wt. % alkylate. The overhead stream from the main product fractionator, about 750,000 lb. of hydrocarbon and HF, is condensed and separated into two phases: an isobutane-rich phase saturated in HF and essentially free of ASO, and an HF phase, saturated in isobutane and essentially free of ASO.

A small side stream removes n-butane from the main product fractionator. The bottoms product, mainly alkylate and ASO, is sent to an alkylate product storage tank. Of the total charge to the product fractionator, the acid-rich feed from the top of the catalyst stripper column typically accounts for about 3.5 to about 4%, and the light ASO fraction typically comprises about 0.7 wt. % of the alkylate product stream withdrawn from the product fractionator.

Changes and modifications in the specifically described embodiments can be carried out without departing from the scope of the invention which is intended to be limited only by the scope of the appended claims.

What is claimed is:

1. A method for separating conjunct polymers which are formed as byproducts of acid catalyzed isoparaffin-olefin alkylation and sulfolane from a mixture containing conjunct polymers, sulfolane, and hydrofluoric acid comprising the sequential steps of:
   (a) alkylating an isoparaffin with an olefin the presence of an alkylation catalyst comprising HF and sulfolane in an alkylation reaction zone whereby ASO byproduct is evolved;
   (b) gravitationally separating effluent from said alkylation reaction zone to provide a less-dense stream containing alkylate product and unreacted isoparaffin and a more dense stream containing sulfolane, ASO, and HF;
   (c) stripping HF from said more dense stream of step (b) with isoparaffin to provide a stripper bottoms stream containing less than about 30 percent hydrofluoric acid weight and a stripper overhead stream containing HF, isoparaffin, and a fraction of said ASO having a lower end boiling point than the ASO containing in said more dense stream of step (b);
   (d) gravitationally separating said stripper bottoms stream into a more dense sulfolane-enriched stream and a less dense conjunct polymer-enriched stream;
   (e) charging said stripper overhead stream to an alkylate product fractionator;
   (f) recovering an overhead stream containing isoparaffin and HF from said alkylate product fractionator;
   (g) recycling said overhead stream of step (f) to said alkylation reaction zone; and
   (h) recovering from said alkylate product fractionator an alkylate product stream containing alkylate gasoline and a fraction of said ASO having a lower end boiling point than the ASO containing in said more dense stream of step (b).

2. The method of claim 1 wherein the isoparaffin of step (c) comprises isobutane.

3. The method of claim 1 wherein said stripping florid comprises at least one selected from the group consisting of isobutane and normal butane.

4. The method of claim 1 wherein said stripping fluid comprises an alkylated product formed by reacting an isoparaffin with an olefin.

5. The method of claim 1 wherein said hydrofluoric acid stripping step (c) provides an intermediate stream containing less than about 25 percent hydrofluoric acid by weight.

6. The method of claim 5 wherein said hydrofluoric acid separation step provides an intermediate stream containing less than about 10 percent hydrofluoric acid by weight.

7. The method of claim 6 wherein said hydrofluoric acid separation step provides an intermediate stream containing less than about 5 percent hydrofluoric acid by weight.

* * * * *

UNITED STATES PATENT AND TRADEMARK OFFICE
CERTIFICATE OF CORRECTION

PATENT NO.   : 5,382,746
DATED        : January 17, 1995
INVENTOR(S)  : J. E. Child et al.

It is certified that error appears in the above-indentified patent and that said Letters Patent is hereby corrected as shown below:

column 8, line 23, after "acid" insert --by-- line 45, "florid" should read --fluid--

Signed and Sealed this

Sixteenth Day of May, 1995

*Attest:*

BRUCE LEHMAN

*Attesting Officer*    *Commissioner of Patents and Trademarks*